United States Patent [19]

Schaper

[11] Patent Number: 5,391,303
[45] Date of Patent: Feb. 21, 1995

[54] POLYETHER POLYAMINO METHYLENE PHOSPHONATE N-OXIDES FOR HIGH PH SCALE CONTROL

[75] Inventor: Raymond J. Schaper, Pittsburgh, Pa.

[73] Assignee: Calgon Corporation, Pittsburgh, Pa.

[21] Appl. No.: 133,488

[22] Filed: Oct. 7, 1993

Related U.S. Application Data

[62] Division of Ser. No. 860,466, Mar. 30, 1992, Pat. No. 5,322,636.

[51] Int. Cl.$^6$ ................................. C02F 5/14
[52] U.S. Cl. .................... 210/700; 210/701; 252/180
[58] Field of Search ............... 210/698–701; 252/180, 181

[56] References Cited

U.S. PATENT DOCUMENTS

| | | | |
|---|---|---|---|
| 2,358,222 | 9/1944 | Fink | 210/697 |
| 2,539,305 | 1/1951 | Hatch | 210/697 |
| 2,783,200 | 2/1957 | Crum et al. | 210/701 |
| 2,980,610 | 4/1961 | Ruchrwein | 210/701 |
| 3,285,886 | 11/1966 | Gunderson et al. | 210/701 |
| 3,434,969 | 3/1969 | Ralston | 210/701 |
| 3,463,730 | 8/1969 | Booth et al. | 210/701 |
| 3,470,243 | 9/1969 | Crutchfield et al. | 260/502.5 |
| 3,483,178 | 12/1969 | Crutchfield et al. | 260/140 |
| 3,514,476 | 5/1970 | Morita et al. | 260/429.9 |
| 3,518,204 | 6/1970 | Hansen et al. | 252/181 |
| 3,816,517 | 6/1974 | Kruger et al. | 260/502.5 |
| 3,928,196 | 12/1975 | Persinski et al. | 210/701 |
| 3,959,361 | 5/1976 | Krueger et al. | 260/502.5 |
| 3,965,027 | 6/1976 | Boffardi et al. | 210/701 |
| 4,080,375 | 3/1978 | Quinlan | 210/700 |
| 4,098,814 | 7/1978 | Sommer et al. | 252/180 |
| 4,110,100 | 8/1978 | Franz et al. | 71/86 |
| 4,457,847 | 7/1984 | Lorenc et al. | 210/698 |
| 4,640,793 | 2/1987 | Persinski et al. | 252/82 |
| 4,650,591 | 3/1987 | Boothe et al. | 210/700 |
| 4,671,888 | 6/1987 | Yorke | 252/180 |
| 4,931,189 | 6/1990 | Dhawan et al. | 210/700 |
| 4,936,987 | 6/1990 | Persinski et al. | 210/699 |
| 4,973,744 | 11/1990 | Hwa et al. | 210/700 |
| 4,977,292 | 12/1990 | Hwa et al. | 210/700 |
| 5,019,343 | 5/1991 | Hwa et al. | 422/16 |
| 5,051,532 | 9/1991 | Hwa et al. | 562/12 |
| 5,069,798 | 12/1991 | Hwa et al. | 210/700 |
| 5,093,005 | 3/1992 | Greaves et al. | 210/700 |
| 5,096,595 | 3/1992 | Hwa et al. | 210/700 |
| 5,259,974 | 11/1993 | Chen et al. | 210/701 |
| 5,262,061 | 11/1993 | Gill et al. | 210/700 |

FOREIGN PATENT DOCUMENTS 432664 12/1990 European Pat. Off. .
437722 12/1990 European Pat. Off. .

OTHER PUBLICATIONS

Wayplex 61-A P.A. Hunt Chemical Corp.
Briquest 221-50A Albright & Wilson Technical Bulletin.

*Primary Examiner*—Peter A. Hruskoci
*Attorney, Agent, or Firm*—Craig G. Cochenour; William C. Mitchell; Michael J. Kline

[57] ABSTRACT

Polyether polyamino methylene phosphonate N-oxides possess high calcium tolerance and have been found to give excellent inhibition of the formation, deposition and adherence of scale-forming salts, especially calcium carbonate, under severe conditions which include elevated pH, high dissolved solids content, and high saturation levels of calcium carbonate.

8 Claims, No Drawings

POLYETHER POLYAMINO METHYLENE PHOSPHONATE N-OXIDES FOR HIGH PH SCALE CONTROL

This is a division of application Ser. No. 07/860,466, filed Mar. 30, 1992, U.S. Pat. No. 5,322,636.

BACKGROUND OF THE INVENTION

1. Field of the Invention

The present invention relates to compositions and methods for inhibiting the formation, deposition and adherence of alkaline earth metal scale deposits, especially calcium carbonate ($CaCO_3$) scale deposits, on metallic surfaces of aqueous systems, especially under conditions of high pH and high calcite concentration, e.g., those found in cycled up cooling systems, where those compositions are polyether polyamino methylene phosphonate N-oxides.

Generally, calcium carbonate scale deposits are incrustation coatings which accumulate on the metallic surfaces of a water-carrying system through a number of different causes.

Various industrial and commercial water-carrying systems are subject to calcium carbonate scale formation problems. Calcium carbonate scale is of particular concern in heat exchange systems employing water, such as, for example, boiler systems, and once-through and open recirculating water cooling systems. Cooling towers are especially significant, particularly where severe conditions, including high pH and high calcite concentrations are encountered.

The water employed in these systems ordinarily will contain a number of dissolved salts, and the alkaline earth metal cation calcium is usually prevalent, as is the anion carbonate. The combination product of calcium cation and carbonate anion will precipitate from the water in which they are carried to form scale deposits when the concentration of the anion and cation comprising the reaction product, i.e., calcium carbonate, exceeds the solubility of the reaction product itself. Thus, when the concentrations of calcium ion and carbonate ion exceed the solubility of the calcium carbonate reaction product, a solid phase of calcium carbonate will form as a precipitate. Precipitation of the reaction product will continue until the solubility product concentrations of the constituent ions are no longer exceeded.

Numerous factors may be responsible for producing a condition of supersaturation for the reaction product calcium carbonate. Among such factors are changes in the pH of the water system, evaporation of the water phase, rate of heat transfer, amount of dissolved solids, and changes in the temperature or pressure of the system.

For cooling systems and similar heat exchange systems including cooling towers, the mechanism of scale formation is apparently one of crystallization of scale-forming salts from a solution which is locally supersaturated in the region adjacent the heating surface of the system. The thin viscous film of water in this region tends to become more concentrated than the remainder of the solution outside this region. Precipitation is also favored on the heat transfer surface because of the inverse solubility relationship of calcium carbonate. As a result, the solubility of the scale-forming calcium carbonate salt reaction product is first exceeded in this thin film, and crystallization of calcium carbonate scale results directly on the heating or heat exchange surface.

In addition to this, a common source of scale in boiler systems is the breakdown of calcium bicarbonate to form calcium carbonate, water and carbon dioxide under the influence of heat. For open recirculating cooling water systems, in which a cooling tower, spray pond, evaporative condenser, and the like serve to dissipate heat by evaporation of water, the chief factor which promotes calcium carbonate scale formation is concentration of solids dissolved in the water by repeated evaporation of portions of the water phase. Thus, even a water which is not scale forming on a once-through basis usually will become scale forming when concentrated two, four, or six times. Moreover, alkalinity of the makeup water, with evaporative cycles over time results in an increasing alkalinity of the water in the overall system, often reaching pH's of 8.5–9.5 and even higher. Conventional scale inhibiting compositions typically fail in systems having such severe conditions.

The formation of calcium carbonate scale deposits poses a serious problem in a number of regards. The calcium carbonate scale which is formed possesses a low degree of heat conductivity. Thus, a calcium carbonate scale deposit is essentially an insulating layer imposed across the path of heat travel from whatever source to the water of the system. In the case of a cooling system, the retarded heat transfer causes a loss in cooling efficiency. In addition to this problem, calcium carbonate scale formation facilitates underdeposit corrosive processes, and a substantial calcium carbonate scale deposit will interfere materially with fluid flow. Consequently, calcium carbonate scale is an expensive problem in many industrial water systems, causing delays and shutdowns for cleaning and removal.

Although the present invention is directed primarily to preventing or inhibiting the deposition of calcium carbonate scale, the most prevalent type of scale deposit, it is also applicable to inhibiting the deposition of other types of alkaline earth metal scales, especially where those are associated with calcium carbonate scale under the severe conditions described herein. For example, most industrial and commercial water contains alkaline earth metal cations, such as calcium and magnesium, and several anions such as bicarbonate, carbonate, and phosphate. When combinations of these anions and cations are present in concentrations which exceed the solubility of their reaction products, precipitates form until their product solubility concentrations are no longer exceeded. These precipitates are alkaline earth metal scales. Thus, by alkaline earth metal scales is meant scales including but not limited to calcium carbonate, magnesium carbonate, and calcium phosphate. These scales form frequently in the tubes of heat exchangers and on other heat exchange surfaces, such as those in cooling towers. Particular systems or applications areas where severe conditions lead to exceptional buildup of calcium carbonate and related scales, in addition to cycled up cooling towers, include reverse osmosis systems, sugar refining evaporators, and certain types of gas scrubbers.

The polyether polyamino methylene phosphonate N-oxides of the present invention are used in the same range of amounts as threshold inhibitors in the scale inhibition method of the present invention, rather than as sequestering or chelating agents, although the compositions of the present invention have dispersant properties as well and significantly reduce the adherency of any scale deposit which is formed, facilitating its easy removal.

Scale-forming compounds can be prevented from precipitating by inactivating their cations with chelating or sequestering agents, so that the solubility of their reaction products is not exceeded. Generally, this requires many times as much chelating or sequestering agent as cation, since chelation is a stoichiometric reaction, and these amounts are not always desirable or economical. However, several decades ago, it was discovered that certain inorganic polyphosphates would prevent such precipitation when added in amounts far less than the concentrations needed for sequestering or chelating.

When a precipitation inhibitor is present in a potentially scale-forming system at a markedly lower concentration than that required for sequestering the scale-forming cation (stoichiometric), it is said to be present in "threshold" amounts. See, for example, Hatch and Rice, *Indust. Eng. Chem.*, 31, 51–53 (1939); Reitemeier and Buehrer, *J. Phys. Chem.*, 44 (5), 535–536 (1940); Fink and Richardson U.S. Pat. No. 2,358,222; and Hatch, U.S. Pat. No. 2,539,305.

Similarly, anionic and cationic polymers can be used as dispersants in accordance with methods known in the art, but the dosage levels necessary to achieve dispersion are in the range of 0.5–1.0% by weight of the system being treated, which is many orders of magnitude higher that the dosage levels used for the compositions of the present invention. Thus, it is a unique aspect of the present invention that it is possible to achieve essentially non-adherent scale using only threshold inhibitor dosage levels of the compositions of the present invention.

Recently, attention has been focused on controlling scaling under severe conditions, where conventional treatments such as those described above do not provide complete scale control. Current technology in scale control can be used to inhibit $CaCO_3$ scale up to 100 to 120 times calcite saturation, i.e., a water containing $Ca^{2+}$ and $CO_3^{2-}$ present at 100 times (100×) their solubility limit. However, what is desired are inhibitors effective in greater than 150× water, especially in greater than 250× water, and more especially in greater than 300× water, i.e., where the calcite ions can be prevented from precipitating as calcium carbonate scale using substoichiometric amounts of an inhibitor. The compositions of the present invention are especially useful under severe conditions characterized by a calcite saturation level of 150× and above, especially 250× and above, and more especially 300× and above, as defined in the paragraph immediately below.

Severity of the scaling tendency of a water sample is measured using the saturation index, which may be derived in accordance with the following equation:

$$SI = \frac{[Ca^{2+}][CO_3^{2-}]}{K_{sp}CaCO_3}$$

where SI is the saturation index for calcium carbonate, $[Ca^{2+}]$ is the concentration of free calcium ions, $[CO_3^{2-}]$ is the concentration of free carbonate ions, and $K_{sp}CaCO_3$ is the conditional solubility product constant for $CaCO_3$. All of the quantities on the right side of the above equation are adjusted for pH, temperature and ionic strength.

Calculation and use of the saturation index, and generation of the data from which it is derived, are matters within the skill of the art. See, for example, *Critical Stability Constants*, Vol. 4: "Inorganic Complexes", Smith & Mantell (1976), Plenum Press; and *Aquatic Chemistry*, Chap. 5, 2nd ed., Stumm & Morgan (1981), Wiley & Sons.

Another characteristic feature of the severe conditions under which the scale controlling compositions of the present invention are especially useful is high pH, i.e. a pH of 8.5 and higher, particularly a pH of 9 or 10 or even higher. A related feature of such severe conditions is high alkalinity.

One of the particular advantages of the scale inhibiting compositions of the present invention is the exceptional calcium tolerances which they exhibit. Calcium tolerance is a measure of a chemical compound's ability to remain soluble in the presence of calcium ions ($Ca^{2+}$). One of the parameters of scale control under severe conditions is pH. As pH increases, calcium tolerance decreases rapidly for traditional $CaCO_3$ threshold inhibitors, e.g., 1-hydroxy ethylidene 1,1-diphosphonic acid (HEDP) and amino tri(methylene phosphonic acid) (AMP). These inhibitors precipitate with calcium at alkaline pH's, rendering them useless as threshold scale inhibitors. While it is common practice to use an acid feed to the water of, e.g., a cooling tower system in order to lower pH and thus avoid the calcium tolerance problem for conventional inhibitors, the danger to handlers which such acid feeding poses makes it all the more important to find scale inhibitors which operate at high pH's.

Another advantage of the scale inhibiting compositions of the present invention is their ability to maintain a level of resistance to degradation by oxidizing biocides which is sufficient to ensure adequate scale inhibition at dosing levels within the ranges herein described. This is of particular importance in cooling systems such as those using cycled up cooling towers. Such systems maintain a large body of water for a considerable length of time exposed to the atmosphere under conditions which do not include sufficient aeration and exposure to sunlight to provide control of microbial, especially bacterial and fungal, growth. Unchecked, such microorganisms flourish and produce colonies extensive enough to give rise to problems of biofilm blockage of heat exchange surfaces, and clogging of the components of the water transporting apparatus used in operating the cooling system.

Such problems of unwanted microbial growth in a cooling system are usually solved by use of an oxidizing biocide, especially chlorine or bromine, since these are inexpensive, effective, and produce minimal environmental impact. However, as is well known, such oxidizing biocides also tend to degrade scale inhibitors containing a N,N-bis(phosphonomethylene) group, presumably by oxidative attack on the nitrogen atom of the group. It has been found that the polyether polyamino methylene phosphonate N-oxides of the present invention offer significant resistance to such degradation, and that they will continue to provide scale inhibition when dosed in accordance with the ranges set out herein.

It is also a surprising attribute of the N-oxides of the present invention that, even though they provide unacceptably low scale inhibition with aqueous systems having normal conditions and scaling tendencies, they provide an unexpectedly high level of scale inhibition protection in aqueous systems characterized by the severe conditions of high pH, high calcite concentration, etc., and having severe scaling tendencies, as described in detail further herein. It was wholly unexpected that compounds having that attribute, would also provide resistance to degradation by oxidizing biocides as well, under the severe conditions and scaling tendencies just described.

BRIEF DESCRIPTION OF THE PRIOR ART

Early efforts to reduce scale formation in water-carrying systems employed compounds such as tannins, modified lignins, algins, and other similar materials. Chelating or sequestering agents have also been employed to prevent precipitation or crystallization of scale-forming calcium carbonate. Another type of agent which has been actively explored heretofore as a calcium carbonate scale inhibiting material is the threshold active inhibitor. Such materials are effective as scale inhibitors in amounts considerably less than that stoichiometrically required, and this amount, as already mentioned, is termed the threshold amount. Inorganic polyphosphates have long been used as such threshold active inhibitors. For examples of such materials, see Fink U.S. Pat. No. 2,358,222; Hatch U.S. Pat. No. 2,539,305; and Ralston U.S. Pat. No. 3,434,969. Certain water soluble polymers, including groups derived from acrylamide and acrylic acid have been used to condition water containing scale-forming calcium carbonate. For example, see U.S. Pat. Nos. 2,783,200; 3,514,476; 2,980,610; 3,285,886; 3,463,730; 3,518,204; 3,928,196; 3,965,027; and 4,936,987. In particular, there has been employed anionic polyelectrolytes such as polyacrylates, polymaleic anhydrides, copolymers of acrylates and sulfonates, and polymers of sulfonated styrenes. See, for example, U.S. Pat. Nos. 4,640,793; 4,650,591; 4,457,847; and 4,671,888. However, when used as threshold alkaline earth metal scale inhibitors, large dosages of these polymers are required, which in turn increases operating costs.

While various polycarboxylates, including polyacrylic acid, have been used as scale inhibiting agents, as described above, no similar use has been made of polycationic agents, apparently because of the difference in electronic charge and the conventional theories of the mechanisms of action for polymeric threshold inhibitors and dispersants.

Neither the polyether polyamino methylene phosphonate N-oxides of the type which comprise the active ingredient of the compositions of the present invention are known, nor is their use for the control of alkaline earth metal scale, particularly calcium carbonate scale, under severe conditions which include elevated pH and high calcium carbonate saturation levels, with enhanced resistance to degradation by oxidizing biocides. Nevertheless, other phosphonates of related structure are known in the art for scale inhibition use.

For example, U.S. Pat. No. 4,080,375 discloses methylene phosphonates of amino-terminated oxyalkylates for use as scale inhibitors, but these compositions are not the same as those of the present invention, nor is there any suggestion that such compositions would be useful under severe conditions as defined herein, where phosphonates such as HEDP and AMP give poor results. U.S. Pat. No. 4,931,189 discloses aminomethylene phosphonates of the type used in the method of the present invention, except that they are not N-oxides, nor is there any suggestion that they might be. Further, the compounds in that patent are only taught to be useful for inhibiting oil field scale formation involving a high brine environment susceptible to gypsum or barite scale formation. Such use in no way suggests the control of scale under the severe conditions described herein under which the compositions and methods of the present invention operate with surprising success.

U.S. Pat. Nos. 4,973,744; 4,977,292; and 5,051,532, as well as EP-A 432 664 and 437 722, all disclose methylene phosphonates which are N-oxides, useful for preventing scale and/or corrosion. There is no teaching or suggestion in any of these references, however, either of the polyether polyamino methylene phosphonate N-oxides of the present invention, or of their surprising effectiveness under the severe conditions of use described herein.

A particular phosphonate which has been marketed for scale control, but apparently not suggested for use under the severe conditions defined herein, is ethanolamine N,N-dimethylene phosphonic acid, sold under such trademarks as WAYPLEX 61-A and BRIQUEST 221-50A.

U.S. Pat. Nos. 4,973,744 and 5,069,798 disclose N,N-bis-phosphonomethyl 2-(hydroxyethoxy)ethylamines and their N-oxides useful as scale inhibitors, but there is no suggestion of the unique compounds of the present invention, nor of their particular usefulness for controlling scale under severe conditions.

Copending application Ser. No. 07/708,527, filed May 31, 1991, discloses polyether polyamino methylene phosphonates for high pH scale control, but these compositions are not N-oxides and lack the surprising stability to degradation by oxidizing biocides exhibited by the compounds of the present invention, and as demonstrated further below.

SUMMARY OF THE INVENTION

The present invention relates to a compound of the formula:

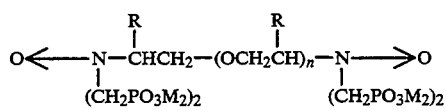

where n is an integer or fractional integer which is, or on average is, from about 2 to about 12, inclusive; M is hydrogen or a suitable cation; and each R may be the same or different is independently selected from hydrogen and methyl. The present invention particularly relates to compounds of the above formula wherein M is hydrogen, R is the same and is methyl, and n is from about 2 to about 4, most preferably about 2.6.

The present invention further relates to a composition useful as a deposit control agent to control the formation, deposition and adherency of scale imparting compounds in an aqueous system, comprising polyether polyamino methylene phosphonate N-oxides of the following formula:

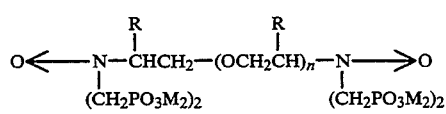

where n is an integer or a factional integer which is, or on average is, from about 2 to about 12, inclusive; M is hydrogen or a suitable cation; and R is the same or different and is independently selected from hydrogen and methyl. Preferably, M is hydrogen, R is the same and is methyl, and n is from about 2 to about 4, most preferably about 2.6.

The present invention also relates to a composition useful as a deposit control agent to control the formation, deposition and adherence of scale imparting compounds in an aqueous system comprising, in combination, polyether polyamino methylene phosphonate N-oxides of the formula above, together with one or more members selected from the group consisting of homo- and copolymers including terpolymers comprising one or more of acrylamide, acrylic acid, 2-acrylamidomethyl propane sulfonic acid, methacrylic acid, itaconic acid, polyether esters of acrylic and methacrylic acids and polyethers based on polyethyleneoxide and polypropyleneoxide and mixtures thereof, including polyethylene glycol monomethacrylate, maleic anhydride, maleic acid, t-butyl acrylamide, sodium styrene sulfonate, sodium vinyl sulfonate, hydroxy propyl acrylate, hydroxy propyl methacrylate, 3-allyloxy-2-hydroxy propane sulfonic acid, sodium salt, and vinyl phosphonic acid, wherein the weight average molecular weight for such polymer additives is in the range of from about 500 to 250,000.

The present invention further relates to a method of inhibiting the formation, deposition and adherence of scale-forming salts in an aqueous system, comprising the step of adding to said system an amount sufficient to establish a concentration of from 1 to 100 mg/L of polyether polyamino methylene phosphonate N-oxides of the formula above. In particular, the present invention relates to such a method in which calcium carbonate is the scale-forming salt, the aqueous system comprises a cooling tower, and said compound is added to the aqueous system being treated in an amount sufficient to establish a concentration of from 10 to 50 mg/L.

The present invention further relates to a method of inhibiting the formation, deposition and adherence of scale-forming salts in an aqueous system, comprising the step of adding to said system an amount sufficient to establish a concentration of from 1 to 100 mg/L of a composition comprising polyether polyamino methylene phosphonate N-oxides of the formula above, together with one or more members selected from the group consisting of: homo- and copolymers including terpolymers comprising one or more of acrylamide (AM), acrylic acid (AA), 2-acrylamide-methyl propane sulfonic acid (AMPSA), methacrylic acid (MAA), ethoxylated methacrylate, itaconic acid (IA), polyether esters of acrylic and methacrylic acids and polyethers based on polyethyleneoxide and polypropyleneoxide and mixtures thereof, including polyethylene glycol monomethacrylate (PGM), maleic anhydride (MA), maleic acid (MA), t-butyl acrylamide (TBAM), sodium styrene sulfonate, sodium vinyl sulfonate, hydroxy propyl acrylate, hydroxy propyl methacrylate, 3-allyloxy-2-hydroxy propane sulfonic acid (AHPS), sodium salt, and vinyl phosphonic acid, wherein the weight average molecular weight for such polymer additives is in the range of from about 500 to 250,000. In particular, the present invention relates to such a method in which calcium carbonate is the scale-forming salt, the aqueous system comprises a cooling tower, said composition is added to the aqueous system being treated in an amount sufficient to establish a concentration of from 10 to 50 mg/L, and said polymer additive is a member selected from the group consisting essentially of 90/10 to 10/90 AA/AMPSA, preferably 75/25 and 60/40 AA/AMPSA, 100 AA, 75/25 SSS/MA, 33/33/34 AA/MAA/IA, 50/50 AA/AM, 70/20/10 AA/AMPSA/PGM-5, 10 and 20 (having 5, 10 and 20 repeating oxyethylene units, respectively), and AA/AMPSA/TBAM.

DETAILED DESCRIPTION OF THE INVENTION

The composition of the present invention useful as a deposit control agent to control the formation, deposition and adherency of scale imparting compounds in an aqueous system comprises polyether polyamino methylene phosphonate N-oxides of the formula:

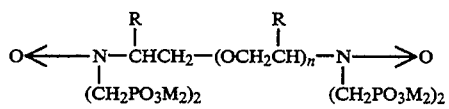

where n is an integer or fractional integer which is, or on average is, from about 2 to about 12, inclusive; M is hydrogen or a suitable cation; and R is the same or different and is independently selected from hydrogen and methyl.

A preferred subclass of compositions of the above formula is that wherein M is hydrogen, R is the same and is methyl, and n is from about 2 to about 4, most preferably about 2.6. In order to obtain high levels of control of scale deposits, especially under the severe conditions defined herein, it has been found that there are certain essential components of the structure of the polyether polyamino methylene phosphonate N-oxides of the present invention which are necessary to provide that performance, and thus clearly distinguish the compositions of the present invention from those of the prior art. For example, the N,N-bis(phosphonomethyl)amino portion of the structure is essential. Whether this group is present initially in the phosphonic acid form or as an alkali metal or other salt of the acid, has no critical bearing on the performance of the overall molecule. At the pH's under which the compositions of the present invention function, they are, and must be, in their ionized form. Thus, it is not critical whether "M" is hydrogen or a suitable cation, and the selection of an appropriate salt form is well within the skill of the art. Alkali metal salts are the most simple, and are preferred for that reason. Overall, however, it is preferred that M is hydrogen.

Another key feature of the polyether polyamino methylene phosphonate N-oxides of the present invention is the N-oxide moiety: N→O. As already described, this group confers significant resistance to degradation by oxidizing biocides, presumably by preventing oxidative attack on the nitrogen atom, of the group.

Another structural feature of the polyether polyamino methylene phosphonate N-oxides useful in the compositions and methods of the present invention is the preferred isopropyl group which bridges the di-phosphonomethylamino group and the polyether group:

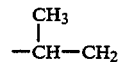

The isopropyl group has been found to provide enhanced scale inhibition activity under the severe conditions defined herein.

Another structural element of the phosphonate scale inhibitors is the polyether moiety. Since the polyether polyamino methylene phosphonates are prepared by phosphonomethylation of the appropriate diamine, the character of the polyether moiety will depend upon the way in which the amine starting material is made. Processes for making such polyether diamines are known in the art; and attention is directed particularly to U.S. Pat. No. 3,236,895, which describes preparation of a variety of polyether diamines especially useful in preparing the phosphonate final products used as deposit control agents in conjunction with the organic sulfonamide stabilizing agents of the present invention.

In accordance with the processes set out in U.S. Pat. No. 3,236,895 and related processes described in the prior art, it is possible to prepare any one of a number of desired polyether diamines within the scope of the present invention. In the general formula for the polyether polyamino methylene phosphonates used herein, the polyether moiety is simply represented by the formula:

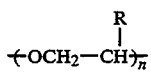

Since R may be hydrogen or methyl, both ethyloxy and propyloxy units are possible. Moreover, R is to be independently chosen, i.e., ethyleneoxy and propyleneoxy units may alternate in various patterns, including blocks of each, or they may be all one or the other. For example, the following are just some of the polyether segments which might be prepared to form the basis for the corresponding diamines, which would then be used to make phosphonates within the scope of the present invention (where EO=ethyleneoxy, and PO=propyleneoxy):

EO; PO; EO—EO; PO—PO; EO—PO; EO—EO—EO;

PO—PO—PO; EO—EO—PO; EO—PO—PO;

EO—PO—EO; PO—EO—PO; EO—EO—EO—EO;

PO—PO—PO—PO; EO—PO—PO—PO;

EO—EO—PO—PO; EO—EO—EO—PO;

EO—PO—EO—PO; EO—PO—PO—EO;

PO—EO—EO—PO

In the above examples, "n" in the main formula would be an integer of from 1 to 4. Since "n" is defined as being from 1 to 12, an even larger number of possible polyether moieties is included. However, it has been found that generally the polyether polyamino methylene phosphonates of lower molecular weight, i.e., where "n" is a smaller integer, are those which provide the greatest amount of scale inhibition under the severe conditions of high pH and high calcite concentration, and thus are those which are preferred. Examples of some of these preferred phosphonates are shown in the table below, where Z=methylenephosphonate:

$$Z_2-N-\overset{R_z}{\overset{|}{C}}HCH_2-(OCH_2\overset{R_a}{\overset{|}{C}}H)_a-(OCH_2\overset{R_b}{\overset{|}{C}}H)_b-NZ_2$$

| Id. No. | a | b | $R_z$ | $R_a$ | $R_b$ |
|---|---|---|---|---|---|
| A | 2 | 1 | $CH_3$ | H | $CH_3$ |
| B | 2.6* | 0 | $CH_3$ | $CH_3$ | — |
| C | 2 | 0 | $CH_3$ | $CH_3$ | — |
| D | 8.5* | 1 | $CH_3$ | H | $CH_3$ |
| E | 5.6* | 0 | $CH_3$ | $CH_3$ | — |
| F | 2 | 0 | H | H | — |
| G | 3 | 0 | H | H | — |
| H | 3 | 0 | $CH_3$ | $CH_3$ | — |
| I | 3 | 1 | H | $CH_3$ | H |
| J | 4 | 0 | H | $CH_3$ | — |

* = value of "n" on average.

It will be noted from the table above that in several cases, "n" has an average value, i.e., the number of repeating ethyleneoxy or propyleneoxy units may vary. Thus, it is possible to have a mixture of varying chain lengths of polyoxyethylene or polyoxypropylene in the final product. This is also contemplated to be within the scope of the present invention, so long as the requirements with respect to the limit of "n" are observed. Consequently, while "n" is merely defined as an integer or fractional integer which is, or on average is, from about 2 to about 12, it has two aspects. It defines the total of the number of repeating ethyleneoxy and/or propyleneoxy units considered separately, and thus if "n" is, e.g., 4, it includes 4 propyleneoxy units, 3 propyleneoxy units and 1 ethyleneoxy unit, 2 propyleneoxy units and 2 ethyleneoxy units, and so forth. The value of "n" may also represent an average number, and this is always the case, of course, when it is a fractional interget. In this case, for each of the ethyleneoxy and/or propyleneoxy units considered separately, mixtures of these units may be present so as to give an average value for "n". For example, in the table above, for Id. No. D, the total of "a" and "b" is 9.5, which is the value of "n". What is described is a mixture of polyether phosphonates in which all of them have an isopropyl bridging group and an ethyleneoxy moiety, but the repeating propyleneoxyunits are such that on average their value is about 8.5.

The number of repeating ethyleneoxy or oxypropylene units, designated by the subscript "n", determines the total molecular weight of the overall polyether polyamino methylene phosphonate or corresponding N-oxide, and thus plays a critical role in determining the scale inhibiting performance of that phosphonate. It has been found that in order to provide adequate scale control under the severe conditions of use defined herein, it is necessary that "n" be an integer or fractional integer which is, or on average is, from about 2 to about 12, inclusive.

As discussed above, the reason for "n" being potentially a fractional integer arises from the fact that the primary diamine from which the polyether polyamino methylene phosphonates are prepared by phosphonomethylation may be a mixture of polyethers in which "n" is two or more of 2, 3, 4, 5 and so forth, in varying proportions. For example, a preferred polyether polyamino methylene phosphonate for use in the compositions and methods of the present invention has a molecular weight of approximately 632 and the value of "n" on average is about 2.6. Thus, this type of polyether phosphonate has a molecular weight distribution, i.e., of the various polyoxypropylenes which make it up, and this distribution is represented by a fractional integer average value for "n". But, it is also within the scope of the present invention for "n" to be a whole integer, e.g., "3", which usually designates a single molecular weight and not a molecular weight distribution.

The polyether polyamino methylene phosphonate N-oxides of the compositions and methods of the present invention are prepared first by phosphonomethylation of the appropriate primary amine which already contains the polyoxypropylene moieties, followed by an oxidation step which provides the N-oxide moieties.

Such primary amine starting materials and their method of preparation are well known. The phosphonomethylation of the primary amine is then carried out by a Mannich reaction such as that described in K. Moedritzer and R. Irani, *J. Organic Chem.* 31(5) 1603–7, "The Direct Synthesis of alpha-Aminomethyl Phosphonic Acids; Mannich-Type Reactions with Orthophosphorous Acid", May 1966. In a typical reaction, the primary amine is added to a mixture of phosphorous acid and water, and concentrated hydrochloric acid is then added slowly, after which the reaction mixture is heated to reflux with addition of aqueous formaldehyde.

Although the general structural formula employed herein indicates that the nitrogen atom is completely phosphonomethylated, as a practical matter, preparation of the polyether polyamino methylene phosphonate N-oxides of the present invention, as described in detail further below, usually results in only about 80 to 90% phosphonomethylation. Other side products give N-substitution with H, $CH_3$, $CH_2OH$, etc. It is not practical, as a matter of simple production economics, however, to isolate and purify the completely phosphonomethylated compounds, since the side products just described do not interfere with scale inhibition. Such side products, are consequently, usually allowed to remain, and the test data set out further below is based on test samples containing such side products. Consequently, the activity levels obtained would be even higher were 100% active compound being tested.

Once the desired phosphonomethylated polyoxypropylene diamine has been prepared as described above, the N-oxide final product of the present invention is then prepared by a step of oxidation, which may be accomplished, e.g., simply by adding hydrogen peroxide to a basic solution of the phosphonomethylated diamine and heating the reaction mixture, which gives high yields of the N-oxide final product. Of course, it is also possible to use other well known techniques for carrying out such a step of oxidation, and any number of these may be successfully employed.

When any of the polyether polyamino methylene phosphonate N-oxide compositions of the present invention are used to inhibit the precipitation, deposition, and adherence of scale-forming salts in an aqueous system, they can be effectively employed for that purpose when added in amounts sufficient to establish a concentration in said aqueous system of from 1 to 100 mg/L. Preferably, the amount added will be sufficient to establish a concentration of from 5 to 75 mg/L, and most preferably, the amount added will be sufficient to establish a concentration of from 10 to 50 mg/L of the composition. It is understood, however, that many factors, of the type which have been explained in detail with regard to the background to the present invention, will determine the actual amount of the polyether polyamino methylene phosphonate N-oxide compositions of the present invention which will be added to any particular aqueous system in order to achieve the maximum amount of inhibition of alkaline earth metal, especially calcium carbonate scale formation, deposition and adherence in that aqueous system. The calculation of those amounts is well within the skill of the artisan in this field.

When the polyether polyamino methylene phosphonate N-oxide compositions of the present invention are used in combination with one or more of the polymers recited further above, the amounts of that combination which must be added in order to inhibit the formation, deposition and adherence of scale-forming salts in an aqueous system, will as a general matter be within the ranges of amounts sufficient to establish the ranges of concentrations of the polyether polyamino methylene phosphonate N-oxides used alone, as recited in detail above. Again, however, calculation of the actual amount is well within the skill of the art.

The phrases "inhibiting the precipitation" and "inhibiting the formation and deposition" are meant to include threshold inhibition, dispersion, solubilization, or particle size reduction. The phrases "inhibiting the adherence" and "increasing the non-adherence", are meant to define the formation of a scale deposit which is easily removed, e.g., by simple rinsing, i.e., a scale deposit which is not so firmly bonded to the surface to which it is attached that it cannot be removed by simple physical means as opposed to harsh mechanical or chemical treatment.

The phrase "scale-forming salts" is meant to include any of the scale-forming salts selected from the group consisting essentially of calcium carbonate, calcium phosphate, calcium phosphonate (including calcium hydroxyethylidene diphosphonic acid), and the corresponding magnesium salts.

The phrase "aqueous system" means commercial or industrial systems utilizing water and involving heat exchange surfaces, usually of metal, including cooling water systems including cooling towers, boiler water systems, desalination systems, gas scrubbers, and thermal conditioning equipment. Of particular importance are those systems which operate under severe conditions as detailed herein, including at least high pH and high calcite concentrations. Typical of such systems are cycled up cooling towers, reverse osmosis systems, sugar refining evaporators, and certain types of gas scrubbers.

The manner of addition of any particular polyether polyamino methylene phosphonate N-oxide composition of the present invention to an aqueous system will also be straightforward to a person of ordinary skill in this art. It may be added in liquid form by mechanical dispensers of known design. It may also be added in diluted liquid form. The polyether polyamino methylene phosphonate N-oxide composition may also be combined with other chemical treatment agents for dispensing to the aqueous system; and these in combination may be dispensed in liquid form.

In the embodiments of the present invention described herein, it has been contemplated that, as a practical matter, only a single polyether polyamino methylene phosphonate N-oxide composition of those described above would be used for the purpose of inhibiting scale. Of course, it would be possible to employ more than one such compound, and that forms a part of the present invention. However, it is also contemplated that one of these compositions not only could be combined, but preferably will be combined with one or more polyelectrolytes so as to provide an even more effective product for the inhibition of scale under the severe conditions described herein.

For example, there could be used in such a combination one or more members selected from the group consisting of homopolymers, copolymers and terpolymers comprising one or more monomers of acrylamide (AM), acrylic acid (AA), 2-acrylamide-methyl propane sulfonic acid (AMPSA), methacrylic acid (MAA), ethoxylated methacrylate, itaconic acid (IA), polyether esters of acrylic and methacrylic acids and polyethers based on polyethyleneoxide and polypropyleneoxide and mixtures thereof, including polyethylene glycol monomethacrylate (PGM), maleic anhydride (MA), maleic acid (MA), t-butyl acrylamide (TBAM), sodium styrene sulfonate (SSS), sodium vinyl sulfonate, hydroxy propyl acrylate, hydroxy propyl methacrylate, 3-allyloxy-2-hydroxy propane sulfonic acid (AHPS), and vinyl phosphonic acid. Weight average molecular weights for such polymer additives should range from about 500 to 250,000.

For example, such compositions include copolymers of 90/10 to 10/90 AA/AMPSA, preferably 75/25 and 60/40 AA/AMPSA. Other preferred polymer additives for use with the polyether polyamino methylene phosphonate N-oxides of the present invention include 100 AA, 75/25 SSS/MA, 33/33/34 AA/MAA/IA, 50/50 AA/AM, 70/20/10 AA/AMPSA/PGM-5, 10 and 20 (having 5, 10 and 20 repeating oxyethylene units, respectively), and AA/AMPSA/TBAM.

Combinations using these polymers together with the polyether polyamino methylene phosphonate N-oxide compositions of the present invention can increase the amount of scale control and deposit control which is achieved under the severe conditions described herein.

EXAMPLES OF PREFERRED EMBODIMENTS

The following examples are presented for the purpose of illustrating the present invention, but are not intended to be in any way a limitation thereof.

EXAMPLE 1

Preparation of

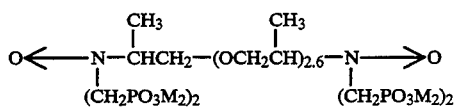

The starting material for this preparation, i.e., the compound of the above formula which is not an N-oxide, was prepared from the corresponding primary diamine by phosphonomethylation in accordance with the method of Moedritzer and Irani, referred to further above, and also as shown in Example 6 below.

The starting material (0.02 mole, 24.69 g) was added to a reaction vessel and the pH was adjusted to 10.00 with a 50% aqueous solution of sodium hydroxide (14.51g). The reaction mixture was then transferred to an Erlenmeyer flask, after which a hydrogen peroxide solution was added dropwise to the reaction mixture (total: 0.044 mole, 4.28g). After several drops were added, the reaction mixture was heated up and then cooled below 15° C. The maximum temperature was 25° C. The reaction mixture was then stirred at room temperature for 17 hours. The desired product was recovered as a 37.90% solution, based on the sodium salt. NMR results indicated 100% conversion of the starting material to N-oxide groups.

EXAMPLE 2

CaCO$_3$ Scale Inhibition at pH 9 and 300X Calcite Saturation—Polyether Polyamino Phosphonate Alone and as the N-Oxide In order to demonstrate the improved scale inhibition performance of the polyether polyamino methylene phosphonate N-oxides used in the method of the present invention, the following procedure was used:

PROCEDURE

Scaling water containing 250 mg/L of $CO_3{}^{-2}$ and 600 mg/L of alkalinity at a pH of 9.0 and 55° C. was used to evaluate scale inhibition performance of test solutions over a 24 hr period. Test solutions were analyzed by withdrawing 10 g of test solution and adding it to the appropriate container through a 0.2μ filter, titrating for calcium, and calculating % inhibition by the Schwarzenbach method.

The results obtained are shown in the table of values below.

TABLE 1

| SAMPLE NO. | DESCRIPTION | % CaCO$_3$ SCALE INHIBITION | | |
|---|---|---|---|---|
| | | 20 ppm | 30 ppm | 50 ppm |
| 1 | Starting material for Exp. 1 | 96 | 99 | 99 |
| 2 | N-oxide of Exp. 1 | 82 | 96 | 99 |

The above results clearly show the surprising level of calcium carbonate scale inhibition under severe conditions with the polyether polyamino methylene phosphonate N-oxide.

EXAMPLE 3

CaCO$_3$ Scale Inhibition at pH 9 and 300X Calcite Saturation—Polyether Polyamino Methylene Phosphonate N-oxides in Combination with Polyelectrolytes Following the test procedures described in Example 2 above, the N-oxide of Sample No. 2 was evaluated in combination with two different polyelectrolytes. The % inhibition was calculated at 24 hours. The results of those evaluations are set out in the table of values below.

TABLE 2

| | % CaCO$_3$ Scale Inhibition with Polyether Polyamino Methylene Phosphonate N-Oxide in Combination with Various Polyelectrolytes | | | |
|---|---|---|---|---|
| SAMPLE NO. | POLYELECTROLYTE | DOSAGE (ppm) | RATIOS OF POLYELECTROLYTE:PHOSPHONATE | |
| | | | 1:1 | 1:4 |
| 3 | 60/40 AA/AMPSA | 50 | 96 | 89 |
| 4 | 70/20/10 AA/AMPSA/PGM-5 | 50 | 95 | 91 |

EXAMPLE 4

Evaluation of Halogen Stability

An assay was conducted in order to determine the level of resistance to degradation by oxidizing biocides, represented by bromine in this case, which is conferred by the presence of the N-oxide moieties. Tests were run in 8 liter cells equipped with pH and temperature control. The water composition used is set out below:

| Ion | mg/L |
|---|---|
| $Ca^{2+}$ | 100 |
| $Mg^{2+}$ | 25 |
| $Na^+$ | 75 |
| $SO_4^{2-}$ | 200 |
| $SiO_2$ | 18 |
| $Cl^-$ | 200 |
| Alkalinity (as $HCO_3$): | |
| for pH 7.5 | 86 |
| pH 8.5 | 309 |

The di-N-oxide of Example 1 was tested at 2 ppm concentration. Halogen levels were determined using the Calgon Field Test for bromine. The bromine stock was made by combining equal molar concentrations of sodium hypochlorite and sodium bromide. The sodium bromide stock solution contained 11.61 g of NaBr per liter, which is equivalent to 8 g/L as chlorine on a molar basis.

For these tests, two milliliters of NaBr and HOCl were combined, resulting in a 4 g/L bromine solution (measured as active chlorine). This solution converts all chlorine to bromine. An aliquot of this solution was then added to the test cell to achieve the desired bromine concentration. During the tests, halogen levels were determined frequently. Additonal slugs of halogen were added when needed to maintain free halogen residuals between 0.4 and 0.6 ppm. Samples were taken at regular intervals for orthophosphate analysis. From these, degradation rates were calculated.

Total and orthophOsphate were analyzed using standard procedures. Total phosphate is the combination of organic and orthophosphate. Total phosphate is determined after digestion by boiling in the presence of acid and persulfate. Orthophosphate determination involves its reaction with ammonium molybdate and antimony potassium tartrate to form an antimony-phosphate-molybdate complex. Both procedures rely on this complex being further reduced by ascorbic acid to produce molybdenum blue. The color intensity is a function of concentration amenable to measurement with a spectrophotometer.

Following the procedures described above, the halogen stability, i.e., the % phosphonate remaining in solution after certain elapsed times, was determined for the starting material and N-oxide of Example 1, i.e., Sample No. 1 and 2, respectively, in Table 1 of Example 2. The results obtained are illustrated in the following table of values.

TABLE 3

Stability of N-Oxide and Non-N-Oxide
In the Presence of 0.5 PPM $Br_2$

| TIME (Hrs.) | % PHOSPHONATE REMAINING IN SOLUTION | |
|---|---|---|
| | NON-N-OXIDE (Sample #1) | N-OXIDE (Sample #2) |
| 0 | 100 | 100 |
| 0.5 | 90 | 93 |
| 1 | 87 | 92 |
| 2 | 84 | 92 |
| 3 | 83 | 91 |
| 4 | 80 | 91 |
| 5 | 79 | 91 |
| 6 | 78 | 91 |
| 7 | 77 | 91 |

EXAMPLE 5

Preparation of Phosphonomethylated Primary Diamine Starting Material of Example 1

A primary diamine having the structural formula:

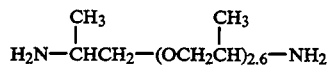

$$H_2N-\underset{\underset{CH_3}{|}}{C}HCH_2-(OCH_2CH)_{2.6}-NH_2$$
(with $CH_3$ substituent)

(56.2 g) was added to a mixture of phosphorous acid (82 g) and deionized water (65 g) in a one liter resin flask fitted with a condenser, a Teflon stirrer, a thermometer and an addition funnel. It is important to maintain as low a level of iron (Fe) in the reaction mixture as possible, and the most likely source of Fe is the phosphorous acid. The Fe interferes somewhat with the reaction, and consequently a low Fe content phosphorous acid is employed.

There was then added slowly to the reaction mixture 50 mL of concentrated HCl. The reaction mixture was subsequently heated to reflux (107° C.). The temperature should be at least 95° C., but the best results are obtained when the reaction mixture is heated to reflux. After the reaction mixture reached reflux, there was added 150 g of 37% aqueous HCHO, which was added dropwise over a period of about 45 min. In order to obtain the best results, the ratio of HCHO to diamine starting material should be at least 4:1 on a molar basis, and preferably somewhat higher, as was the case in this synthesis.

The reaction mixture was then refluxed for an additional period of 3 hrs. While the reaction time depends upon temperature, best results are obtained by refluxing for at least ½ hr, preferably 2 to 3 hrs.

The reaction mixture was then cooled, and 97.2 g of volatiles were stripped off at 50° C. using a rotary evaporator. A total of 303.4 g of product was obtained, with a theoretical activity of 48%. $P^{31}$ NMR indicated that at least about 90% of the —NH groups has been phosphonomethylated. Impurities included unreacted phosphorous acid, formaldehyde, phosphoric acid, methanolphosphonic acid, and other unidentified phosphorous compounds.

It has been found that the scale control performance of the polyether polyamino methylene phosphonate N-oxides of the present invention depends to some extent, although not a very significant extent, on the variations in the process parameters described above. Best results are obtained, consequently, by employing the optimum conditions as outlined above.

What is claimed is:

1. A method of inhibiting the formation, deposition and adherence of scale-forming salts including calcium carbonate in an aqueous system characterized by high pH and high calcite saturation levels wherein the pH is at least 8.5 and the calcite saturation level is at least 150 times the solubility limit of calcium as calcite, comprising the step of adding to said system an amount sufficient to establish a concentration of from 1 to 100 mg/L of a composition comprising polyether polyamino methylene phosphonate N-oxides of the formula:

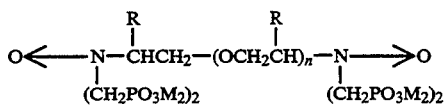

where n is an integer or fractional integer which is, or on average is, from about 2 to about 12, inclusive; M is hydrogen or a cation of an alkali metal salt; and each R may be the same or different and is independently selected from hydrogen and methyl.

2. A method according to claim 1 wherein said N-oxide composition is added to the aqueous system being treated in an amount sufficient to establish a concentration of from 10 to 50 mg/L.

3. A method according to claim 1 wherein for the composition, M is hydrogen, each R is methyl, and n is about 2.6.

4. A method of inhibiting the formation, deposition and adherence of scale-forming salts including calcium carbonate in an aqueous system characterized by high pH and high calcite saturation levels wherein the pH is at least 8.5 and the calcite saturation level is at least 150 times the solubility limit of calcium as calcite, comprising the step of adding to said system an amount sufficient to establish a concentration of from 1 to 100 mg/L of a composition comprising polyether polyamino methylene phosphonate N-oxides of the following formula:

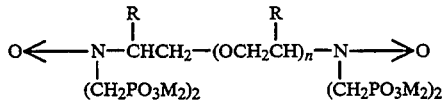

where n is an integer or fractional integer which is, or on average is, from about 2 to about 12, inclusive; M is hydrogen or a cation of an alkali metal salt; and each R may be the same of different and is independently selected from hydrogen and methyl;

TOGETHER WITH one or more
homopolymers, copolymers and terpolymers comprising one or more monomers of acrylamide (AM), acrylic acid (AA), 2-acrylamidemethyl propane sulfonic acid (AMPSA), methacrylic acid (MAA), ethoxylated methacrylate, itaconic acid (IA), polyether esters of acrylic and methacrylic acids and polyethers based on ethyleneoxide and propyleneoxide and mixtures thereof, polyethylene glycol monomethacrylate (PGM), maleic anhydride (MAH), maleic acid (MA), t-butyl acrylamide (TBAM), sodium styrene sulfonate (SSS), sodium vinyl sulfonate, hydroxy propyl acrylate, hydroxy propyl methacrylate, 3-allyloxy-2-hydroxy propane sulfonic acid (AHPS), and vinyl phosphonic acid, wherein the weight average molecular weight for such polymer additives is in the range of from about 500 to 250,000.

5. A method according to claim 4 wherein for the N-oxide composition, M is hydrogen, each R is methyl, and n is about 2.6.

6. A method according to claim 4 wherein the polymer additive is selected from the group consisting of polyacrylic acid and copolymers of AA/AMPSA, SSS/MA, AA/MAA/IA, AA/AM, AA/AMPSA/PGM having 5 repeating oxyethylene units, and AA/AMPSA/TBAM.

7. A method according to claim 6 wherein said N-oxide and said polymer additive are together added to the aqueous system being treated in an amount sufficient to establish a concentration of from 10 to 50 mg/L.

8. A method according to claim 7 wherein the aqueous system being treated is a cooling system.

* * * * *